United States Patent
Zhu et al.

(10) Patent No.: US 12,371,351 B2
(45) Date of Patent: Jul. 29, 2025

(54) PROTONATED SMALL-MOLECULE DRINKING WATER, PREPARATION METHOD AND APPLICATION

(71) Applicant: Hangzhou Shanshangshui Technology Co., Ltd, Hangzhou (CN)

(72) Inventors: Yixin Zhu, Hangzhou (CN); Tingting Lu, Hangzhou (CN)

(73) Assignee: Hangzhou Shanshangshui Technology Co., Ltd, Zhejiang (CN)

( * ) Notice: Subject to any disclaimer, the term of this patent is extended or adjusted under 35 U.S.C. 154(b) by 461 days.

(21) Appl. No.: 17/642,421

(22) PCT Filed: Sep. 3, 2020

(86) PCT No.: PCT/CN2020/113125
§ 371 (c)(1),
(2) Date: Mar. 11, 2022

(87) PCT Pub. No.: WO2021/077913
PCT Pub. Date: Apr. 29, 2021

(65) Prior Publication Data
US 2022/0363573 A1    Nov. 17, 2022

(30) Foreign Application Priority Data
Oct. 22, 2019    (CN) .......................... 201911005058.4

(51) Int. Cl.
*C02F 1/48*    (2023.01)
(52) U.S. Cl.
CPC ...................... *C02F 1/48* (2013.01)
(58) Field of Classification Search
CPC ............... A23L 2/68; A61P 1/16; C02F 1/005
See application file for complete search history.

(56) References Cited

U.S. PATENT DOCUMENTS

| 8,651,015 B2 | 2/2014 | Zhu et al. |
| 8,674,294 B2 | 3/2014 | Zhu et al. |

(Continued)

FOREIGN PATENT DOCUMENTS

| CN | 100482598 C | 4/2009 | |
| CN | 101610679 A | * 12/2009 | ............. A01N 59/16 |

(Continued)

OTHER PUBLICATIONS

Joseph et al—CN 101610679 A machine translation—Dec. 23, 2009 (Year: 2009).*

(Continued)

*Primary Examiner* — Bradley R Spies
(74) *Attorney, Agent, or Firm* — BainwoodHuang

(57) ABSTRACT

Drinking water, which specifically refers to proton-attached small-molecule drinking water, a preparation method therefor and an application occasion thereof. Small-molecule cluster water thereof is formed by distributing two to six water molecules around one H+. The small-molecule cluster water is atomized by running ordinary water through an atomizing device (30); the water is passed through an atomized water channel (60), sent to a hydrogen ion generating region (50), and is then mixed in a hydrogen ion and water vapor mixing region (150) of a mixing device (40). The advantages are: the small-molecule drinking water has a stable structure, and may be stored for a long time; the preparation method may be large-scale and has a wide range of practical application value; and drinking the small-molecule drinking water has a good effect on improving human health.

13 Claims, 7 Drawing Sheets

(56) References Cited

U.S. PATENT DOCUMENTS

| | | | |
|---|---|---|---|
| 9,972,481 B2 | 5/2018 | Zhu et al. | |
| 10,062,559 B2 | 8/2018 | Zhu et al. | |
| 10,701,961 B2 | 7/2020 | Zhu et al. | |
| 2010/0057199 A1* | 3/2010 | Guggenbichler | C01G 39/02 |
| | | | 604/265 |
| 2010/0096270 A1 | 4/2010 | Nabeshima | |
| 2013/0009055 A1* | 1/2013 | Zhu | H01J 49/16 |
| | | | 250/288 |
| 2017/0117126 A1* | 4/2017 | Zhu | H01J 49/164 |

FOREIGN PATENT DOCUMENTS

| | | |
|---|---|---|
| CN | 201888009 U | 6/2011 |
| CN | 202142497 | 2/2012 |
| CN | 206204073 | 5/2017 |
| TW | 201714529 A | 5/2017 |
| TW | M612412 U | 5/2021 |
| WO | 2008117387 | 2/2008 |

OTHER PUBLICATIONS

Zheng—CN 206204073 U machine translation—May 31, 2017 (Year: 2017).*

Hammer et al., Nathan I.; "How Do Small Water Clusters Bind An Excess Electron" (Oct. 2004, Science, vol. 306, No. 22, p. 675), 6 pages.

Li-Fuzhi, Zhang, Xiaojian, Zheng. Environmental Scientific Report, 2004, 24 (1): 6-9). Original.

Li-Fuzhi, Zhang, Xiaojian, Zheng. Environmental Scientific Report, 2004, 24 (1): 6-9). English Translation.

Xiuguang, Lin. "Die of Water." Yuanfang Press; 1990 (ISBN7-80595-543-3) (excerpts with selected translations).

Botti A. et al: "Eigen versus Zundel complexes in HCl-water mixtures", The Journal of Chemical Physics, vol. 125, No. 014508, Jul. 7, 2006, pp. 0-9, XP093088199, US ISSN: 0021-9606, DOI: 10.1063/1.2212421 Retrieved from the Internet: URL: https://pubs.aip.org/aip/jcp/article-pdf/doi/10.1063/1.2212421/147559820/014508_1_online.pdf.

Botti A et al: "Solvation shell of H+ ions in water", Journal of Molecular Liquids, Elsevier, Amsterdam, NL, vol. 117, No. 1-3, Mar. 15, 2005, pp. 77-79, XP027777881, ISSN: 0167-7322 (retrived on Mar. 15, 2005).

Headrick Jeffrey M. et al: "Spectral Signatures of Hydrated Proton Vibrations in Water Clusters", Science, vol. 308, Jun. 17, 2005, XP093088223, US ISSN: 0036-8075, DOI: 10.1126/science.1111307.

Klein Roger A. et al.: "Ab Initio Calculations of 17 O NMR-Chemical Shifts for Water. The Limits of PCM Theory and the Role of Hydrogen-Bond Geometry and Cooperativity", The Journal of Physical Chemistry A, vol. 108, No. 27, Jun. 16, 2004, pp. 5851-5863, XP093088240, US ISSN: 1089-5639, DOI: 10.1021/jp0487408.

* cited by examiner

| ¹⁷O-Half peak width of Wahaha purified water under different magnetic field intensities | | |
|---|---|---|
| Magnetic Field Intensity /Gauss | Time /min | Half Peak Width /Hz |
|  | 5 | 80.81 |
| 1000 | 5 | 79.10 |
| 2000 | 5 | 79.20 |
| 3000 | 5 | 80.64 |
| 4000 | 5 | 77.34 |
| 5000 | 5 | 79.95 |
| 6000 | 5 | 79.61 |
| 7000 | 5 | 79.79 |

| Variation of ¹⁷O-Half peak width of Wahaha purified water with temperature | |
|---|---|
| Temperature /°C | Half Peak Width /Hz |
| 26°C | 91.00 |
| 36°C | 71.58 |
| 46°C | 67.32 |
| 56°C | 54.04 |
| 66°C | 50.54 |
| 76°C | 45.64 |
| 86°C | 44.46 |

PROTONATED SMALL-MOLECULE DRINKING WATER, PREPARATION METHOD AND APPLICATION

TECHNICAL FIELD

The invention relates to drinking water, in particular to proton-attached small-molecule drinking water as well as a preparation method and application occasions thereof.

BACKGROUND OF THE INVENTION

Water is vital for life. Human tissue is composed mainly of water, and water is used for promoting digestion, regulating body temperature, metabolic waste, and transportation of nutrition and the like on the human body. The quality of water, to a large extent, determines the health of the human body, so it is very important to drink healthy water. In nature, water cannot exist in a monomolecular state, and water cannot be found in the form of a structured small molecule group. In general, natural water is found in a water molecule group composed of 13-16 water molecules, and may be composed of 5-7 or even fewer water molecules. In small molecular mass water, permeability is strong and super-strong biological permeability is achieved. The cell membrane can be easily penetrated, such that oxygen, nutrients, minerals and trace elements can be transported into cells. At the same time, water attaches easily to toxins and wastes of the cells in the body. In "hydration," the wastes can be discharged from the body, which can effectively improve the activity of biological cells. Clusters of water molecules are random, amorphous, chain-like clusters. Their solubility and permeability are very low, so they are not easily absorbed by animals, plants, and people. How to make macromolecular water into small water clusters for human use is a subject that the applicant and technical personnel in the field are committed to research and overcome.

Water exists in a certain structural form, and atoms are connected by covalent bonds. Just like people like "groups," water molecules also like "groups." They are attracted to each other by means of hydrogen bonds to form clusters, just like clusters of organisms. Therefore, scientists have named them "small-molecule water." The greater the number of water molecules in a water cluster, the lower the energy level. In most cases, especially in the case of long-term static conditions, water can form clusters of up to dozens of water molecules. These macromolecular clusters are random, like some chain-like thread clusters. Their solubility and permeability are very low. They are not easily absorbed passively by plants and people. They become "stagnant water." We call this kind of water macromolecular cluster water. Ordinary tap water is macromolecular cluster water, which is held together by more than 13 water molecules.

Under certain physical and chemical conditions, the hydrogen bonds between water molecules can be partially broken, so as to create "small-molecule water" with only a few water molecules linked together. Small-molecule water also exists in nature, and long-term effects of the earth's magnetic field can break the clusters of macromolecular water into small-molecule water. Artificial methods can be used to "break clusters," such as passing water through an electromagnetic field, a special frequency spectrum field, or a nano material container. Small-molecule water is palatable and tasty, is easily absorbed by the human body, and can even treat many diseases, which is very beneficial to human health.

At present, nuclear magnetic resonance spectroscopy is used to measure the half-peak width of water, which can reflect the cluster structure of liquid water. Generally speaking, the larger the half-peak width, the larger the cluster of water molecules. Likewise, the smaller the half-peak width, the smaller the cluster. The half-peak widths from nuclear magnetic resonance spectra of different qualities of water are different. For example, the half-peak width of surface water polluted by organic matter is 145 Hz, the half-peak width of tap water and purified water is generally above 100 Hz, and the half-peak width of high-quality ice spring water is 50-70 Hz. The smaller the half-peak width of water, the fewer water molecules in the "group," the stronger the activity of the water molecules, and the stronger the physiological function in the human body (Reference Document: Li-Fuzhi, ZHANG, Xiaojian, Zheng). The cluster structure of liquid water is studied with $^{17}O$ nuclear magnetic resonance. Environmental Scientific Report, 2004, 24 (1): 6-9).

Small-molecule water mainly has the following effects: 1. Improves the hydration of cells: The cell membrane water channel is a very narrow channel (the diameter of the narrowest part of the water channel is 2.8 angstroms and the length is 2 nanometers). The shape of the water channel is similar to that of an hourglass. Not all water can pass into and out of the cells smoothly through the water channel of the cell membrane but is related to the size of the water molecular cluster. The smaller the molecular mass of water, the higher the activity of water, the stronger the permeability is, and the easier it is to pass through the water channel of the cell membrane. Therefore, the type of water that people drink is important. Common tap water is generally a "water cluster" consisting of more than 13 single molecules. These water molecules are relatively difficult to absorb by water channels of the cell membrane. Small-molecule water composed of about 2 to 6 water molecules (our test results show that protonated small-molecule drinking water produced by us contains the highest composition of two water molecules) have strong permeability and solubility, and is easier to get into and out of cells to achieve full hydration. Through hydration, cells can absorb nutrients and discharge metabolites, thus becoming the "life water" that cells really need. 2. Increase the solubility of nutrients and drugs: the viscosity and surface tension of water play an important role in the dissolution of vital substances and drugs. Water with relatively low surface tension can not only carry more nutrients into cells, but also can discharge more waste and poisons out of cells. This is the material basis of the detoxification function of life. Due to the change of structure, the surface tension of the small molecule water becomes smaller, reaching half of that of distilled water. It can improve the solubility of active ingredients of certain nutrients and drugs with specific structures. In this regard, scientists have done a lot of experiments, comparing the solubility of common water and small-molecule water in Chinese and Western medicine, proving that the solubility of small-molecule water is significantly higher than that of ordinary water. This may also be one of the reasons that small-molecule water has medical and health effects.

Due to the above characteristics of small-molecule water, it can ensure and promote the healthy survival and growth of cells and play normal physiological functions.

A toxin is a substance that can interfere with normal physiological activities and destroy body functions. Examples of intrinsic toxins include free radicals, cholesterol, fat, uric acid, lactic acid, toxic water, and congestion.

The intestinal tract is the largest detoxification organ of the human body and undertakes most of the body's detoxification tasks. The intestinal tract itself is full of folds and is the site of most toxins and metabolites in the human body. However, modern people's diet is too delicate and irregular, having food safety and other problems. Given the longer and curved intestinal tract of Asian people, it is easy to hide toxins in the intestinal tract, and the toxin retention time is more than 72 hours. The largest detoxification organ has thus become a large base for storing pollutants and dirt. Intestinal toxins are also known to be a source of diseases and are one the main culprits in obesity. Studies have shown that women with swimming circles, small belly, abdominal fat, and other problems have varying degrees of intestinal toxin accumulation, causing various health problems. Therefore, a core objective of detoxification is to improve intestinal peristalsis and constipation.

In nature, water exists in the form of a molecular structure. A water molecule is composed of two hydrogen atoms and one oxygen atom. The two hydrogen atoms are not linearly connected with the oxygen atom at 180 degrees but rather are distributed in a V shape. In the three different phases of water, the angles formed between the two hydrogen atoms and the oxygen atom are also different. In the hydrogen bond (H—O) of the water molecule, due to the strong electronegativity of the oxygen atom, the shared electron pair is strongly biased to one side of the oxygen atom, so that the proton of the hydrogen atom is relatively "exposed." In this way, multiple water molecules can be connected together with hydrogen bonds, and multiple water molecules can be connected together with hydrogen bonds to form macromolecular water with a cage structure. The research shows that by reducing the large molecular water clusters with cage structures to form small-molecule water, the solubility, permeability, metabolism, diffusion, and emulsifying power of water can be enhanced, thus having a certain "activation" effect, and enhancing the metabolism, lipid metabolism, enzyme activity, and immune function of organisms to a certain extent. Such water is also called "activated water." Davey et al. found that in the nucleosome, a hydrogen bridge is formed between protein and DNA by means of hydrogen bonding with water molecules to maintain the spatial configuration of the protein-DNA. The structure of the water can help to explain the transformation mode of the three-dimensional conformation of DNA connected with protein. The interaction between proteins and solvents plays an important role in determining the conformation and stability of natural proteins. Therefore, studying the effect of water on protein stability provides important information for understanding the conformation of the natural protein and the folding and stretching of the peptide chain. At present, many scientists pay more attention to the binding effect of water molecules with proteins and amino acids in proteins. For example, Zhao Lin proposed that water in small-molecule water easily forms a stable six-ring or six-cage-shaped water structure around it during the hydration of lysozyme, thus strengthening the force for maintaining the three-dimensional structure of lysozyme and other proteins and enhancing the thermal stability of lysozyme. In 2004, the world authoritative journal Science published an article entitled "How Do Small Water Clusters Bind An Excess Electron" (October 2004, Science, Vol. 306, No. 22, P. 675), which showed how to bond excess electrons in small-molecule water theoretically. The root cause of the water molecules forming a cluster is that a large number of hydrogen bonds are formed between water molecules. The nature of the hydrogen bonds is that a hydrogen atom in the water molecule has an empty orbital that lacks electrons. If an excess of electrons exists in the water, the hydrogen atoms' empty orbitals preferentially combine with the electrons, and the hydrogen bonds between the water molecules are reorganized, allowing the formation of large water molecular clusters to be achieved. Based on the above theory, a series of preparation methods of small-molecule water, or active water, have been developed. The typical methods are as follows: (1) an electromagnetic method; test results of which are shown in FIG. 2; (2) a mechanical method such as centrifugation and the like; (3) an ultrasonic method; (4) a far infrared method; (5) a functional ceramic method; and (6) an information template method, such as Lorenzen water in the United States. Under guidance of the above theory, there are many methods for the preparation of small-molecule water. However, due to the basic use of macro physical methods, it is difficult to form small-molecule water with good uniformity at the molecular level. For example, Lorenzen small-molecule water in the United States is required to be stored at lower than 4° C. for 3-6 months at most. Secondly, some methods, such as the Lorenzen process, cannot be deployed for large-scale production due to equipment. Therefore, the above-mentioned production of small-molecule water is still based on theory and at small experimental stages and cannot be applied in industry. Small-molecule water is still far away from our life and are not understood and utilized by many people. Therefore, there is an urgent need to develop an industrialized method for the preparation of small-molecule water. The small-molecule water obtained by a traditional heating method is shown in FIG. 3.

The small-molecule water theory is a concept proposed by Lin Xiangxiu, M D, who began studying small-molecule water in 1985 and wrote a book in 1990. The structure of ordinary natural water is a cluster of large molecules synthesized by association of 100~200 water molecules. Hydrogen in one water molecule attracts oxygen in another water molecule, forming a chain structure of hydrogen bonds. After natural water is subjected to sufficient magnetic treatment, hydrogen bonds are cut to form many small molecular clusters. Because its shell is cut open, many protonated small-molecule water are formed and electrons can be released. Then, according to physical testing, water ion concentration is high, resulting in so-called ionized water rich in small-molecule water, referred to as small molecules of water. This structure of a water molecule group is a dynamic combination, and its stable existence time is only about $10\text{-}12\times10^{-12}$ seconds, which means that some water molecules are constantly added to a water molecule group. Some of the water molecules leave the water molecules, and the group size is just an average. At room temperature, the average water molecule size is about 30 to 40 water molecules. The structure of small-molecule water is shown in FIG. 1.

SUMMARY OF THE INVENTION

Aiming at the defects in the prior art, the invention provides small-molecular water which is different from the traditional small-molecular water, and the preparation method also differs from the existing preparation method.

The technical scheme of the invention is as follows:

The small molecule drinking water is characterized in that common water contains one or more of the following small-molecule water; the specific structure being as shown in FIG. 10.

Small molecular cluster water is formed by 2-6 water molecules distributed around an H+, where O is an oxygen atom in a water molecule, H is a hydrogen atom in a water molecule, and H+ is a hydrogen ion with positive charge. The small molecular cluster water in the present application differs from the traditional small molecular water structure. The traditional small molecule water includes water molecules connected by means of hydrogen bonds; only the number of water molecules is fewer. Due to the presence of hydrogen bonds, the small molecular water cannot be stored at normal temperature for a sufficient time, and the actual usefulness is lost, as shown in FIG. 1. In the present application, a relatively stable small molecular cluster water is formed by providing water molecules around a positively charged hydrogen ion, instead of a group formed by hydrogen bonds. The energy of the hydrogen ions changes the structure of the water molecules, and the hydrogen bond energy of the water molecules is counteracted, thereby ensuring the long service life of the proton-attached small molecular cluster water, and achieving the biological function.

Preferably, the ordinary water in the small-molecule drinking water is purified water, and has a better effect.

Preferably, the small molecule drinking water contains H+ in a concentration of not less than $10^{-6}$ mol/L. Compared with the structure characteristics of the small and medium molecular drinking water in the application that have not been recognized in the prior art, the concentration has a more beneficial effect on the human body.

The preparation method includes the following steps: atomizing ordinary water through an atomization device to generate atomized water vapor, feeding the atomized water vapor into a hydrogen ion generation region through an atomization water channel, placing a needle tip of a hollow launch needle in the hydrogen ion generation region, generating a strong electric field at the needle tip of the hollow emission needle, performing ionization on the atomized water vapor to form a positively charged hydrogen ion, mixing hydrogen ions and water vapor in a hydrogen ion and water vapor mixing area of the mixing device; and conveying the mixed water to an attached protonated water packaging device to obtain small-molecule drinking water with two, three, four, five, or six water molecules attached around a positively charged hydrogen ion. The mixing device is divided by a perforated cathode into a hydrogen ion generation region and a hydrogen ion and water vapor mixing area. In the present application, purified water in a water storage tank is fed into the hollow emission needle by means of the miniature infusion pump, and the purified water is charged by the strong electric field at the tip to form hydrogen ions. As the radius of the hydrogen ions is extremely small, a powerful electric field is formed. In the mixing area, water molecules of the atomized water are adsorbed, thereby forming 2, 3, 4, 5, and 6 small molecular groups of water attached to respective protons, and the small molecular mass water is attached, so that the small molecular group water has hydrogen ion energy. Due to the existence of the electrostatic energy of the hydrogen ions, the attached proton small molecular group water has a life of more than 4 days.

Preferably, the ordinary water in the preparation method of the small-molecule drinking water is purified water, the purified water is put into a sterile water storage tank, and the purified water enters the atomization device for atomization through the sterile infusion pump.

Preferably, the hydrogen ion generation in the preparation method of the small molecule drinking water includes the following steps: feeding raw material for hydrogen ion generation into the hydrogen ion generation region through a pump body, wherein a needle tip of the hollow emission needle is placed in the hydrogen ion generation region, a strong electric field is generated at the emission tip, hydrogen is ionized to form positively charged hydrogen ions, and the other end of the needle tip of the hollow emission needle is connected with the water storage tank.

Preferably, in the preparation method of the small-molecule drinking water, a temperature above 80 deg-C. is maintained in the atomization device and the internal space of the mixing device.

Preferably, in the preparation method of the small molecule drinking water, the hydrogen ion generation region and the micro infusion pump deliver purified water from the water storage tank to the needle tip of the hollow emission needle. The needle tip of the hollow emission needle and the perforated cathode (120) are supplied with voltage by a high-voltage power supply (90), a strong electric field is generated at the needle tip of the hollow emission needle, and water molecules at the needle tip of the hollow emission needle are ionized to form positively charged hydrogen ions.

Application of small-molecule drinking water includes treatment of metabolic diseases, such as diabetes, blood fat lowering, liver protection, and blood uric acid reduction in the body.

The small-molecule drinking water has the beneficial effects that the small-molecule drinking water has a stable structure and can be preserved for a long time. The preparation method can be performed on a large-scale and has wide practical application. Also, drinking of small-molecule water has a good improvement effect on human health.

Figure 1:
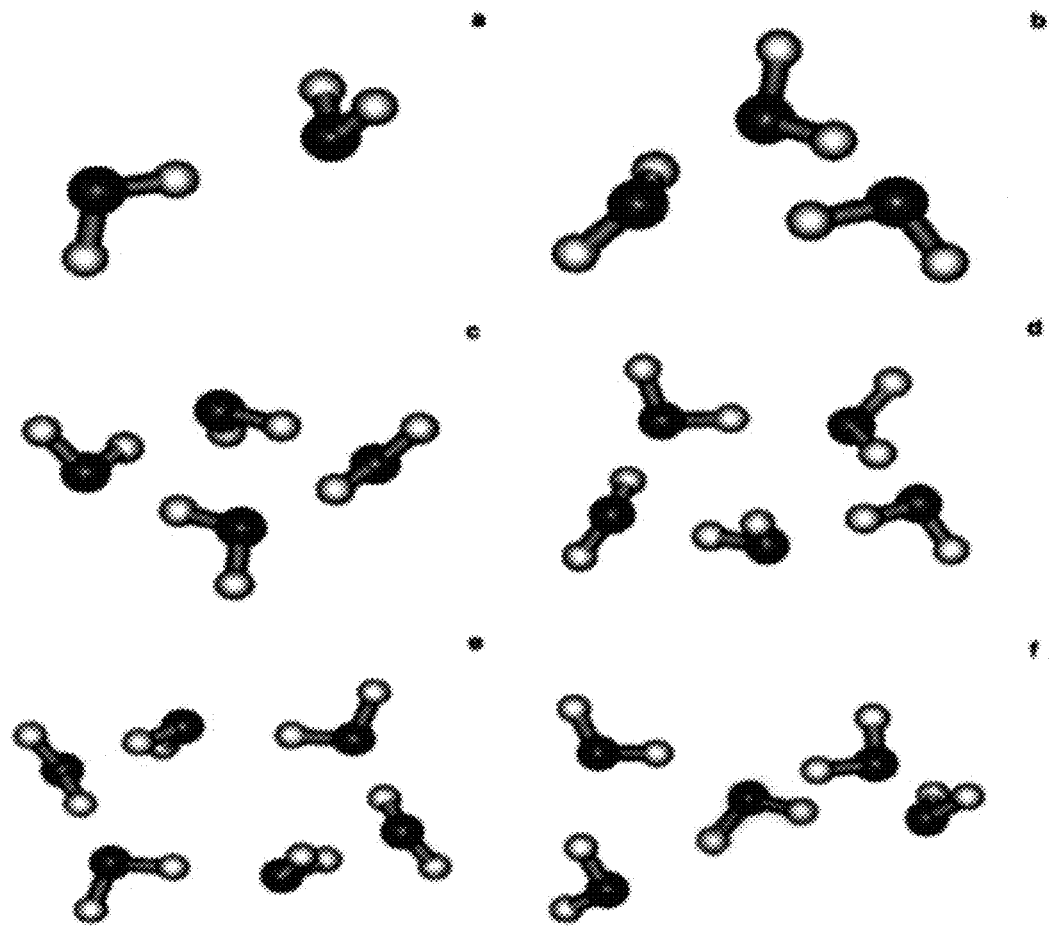
FIG. 1 is a structure diagram of traditional small molecular cluster water.
Figure 2:
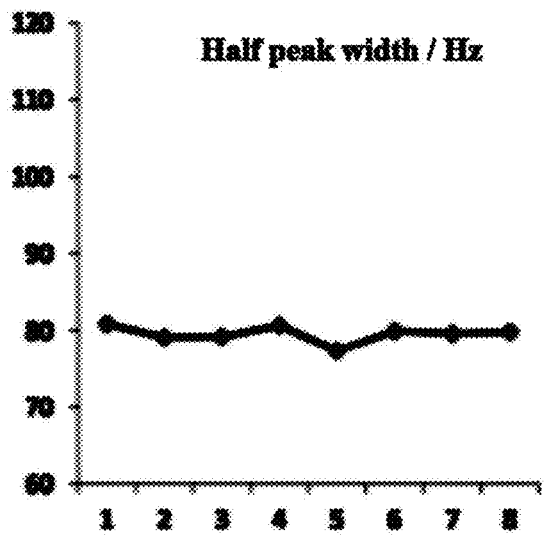
FIG. 2 is a magnetic resonance (NMR)$^{17}$O of detection results after applying a strong magnetic field to water.
Figure 3:
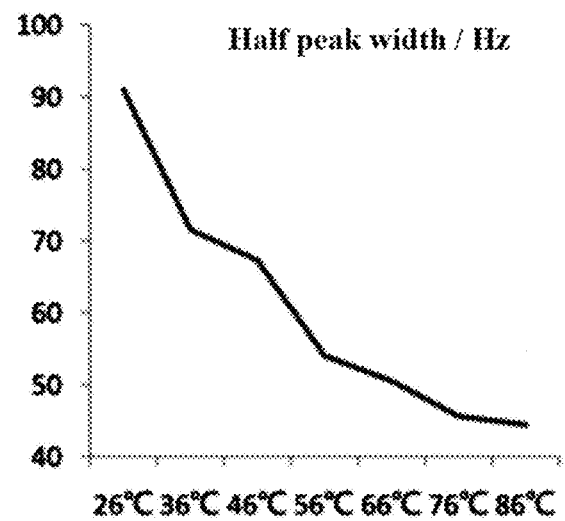
FIG. 3 is a magnetic resonance (NMR)$^{17}$O of detection results after heating water.

In the drawings, larger dark circles represent oxygen atoms in a water molecule, smaller light circles represent hydrogen atoms in a water molecule, and smaller light circles with an "H" in the center and a "+" to the upper-right represent hydrogen ions with positive charge.

DETAILED DESCRIPTION OF THE EMBODIMENTS

Embodiment 1

Figure 4:
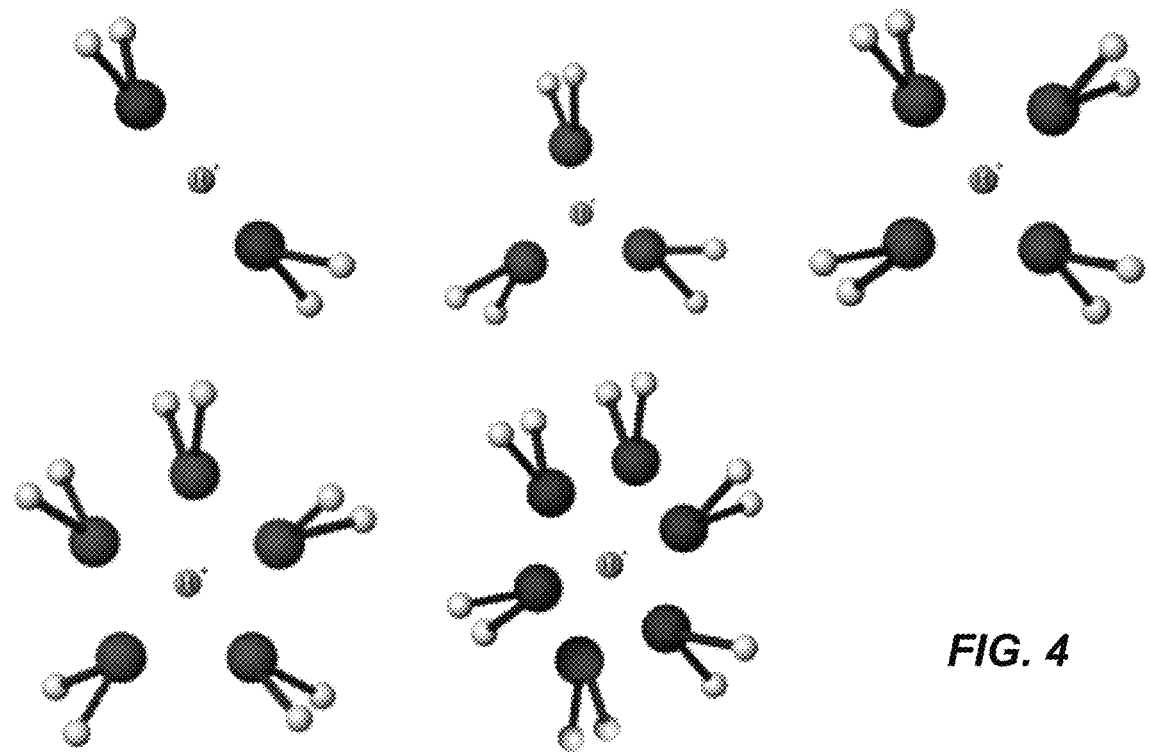
FIG. 4 is a structural schematic diagram of small-molecular cluster water according to the present invention.
Figure 5:
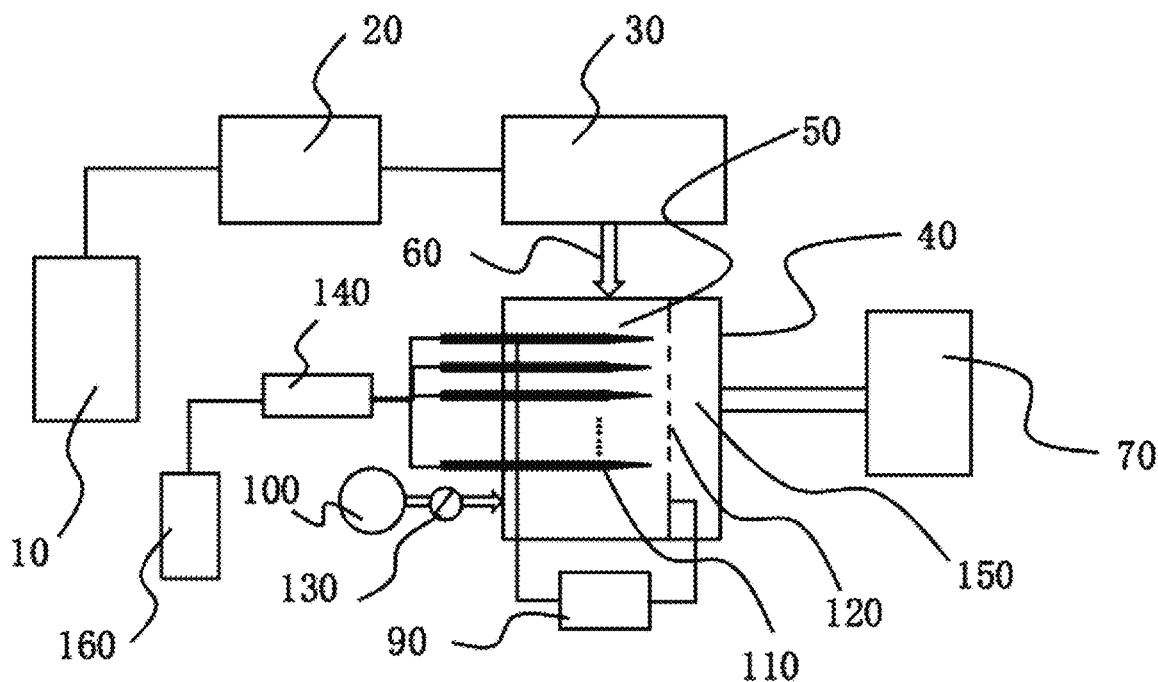
FIG. 5 is a schematic diagram of an apparatus for a preparation method of the present invention.
Figure 6:
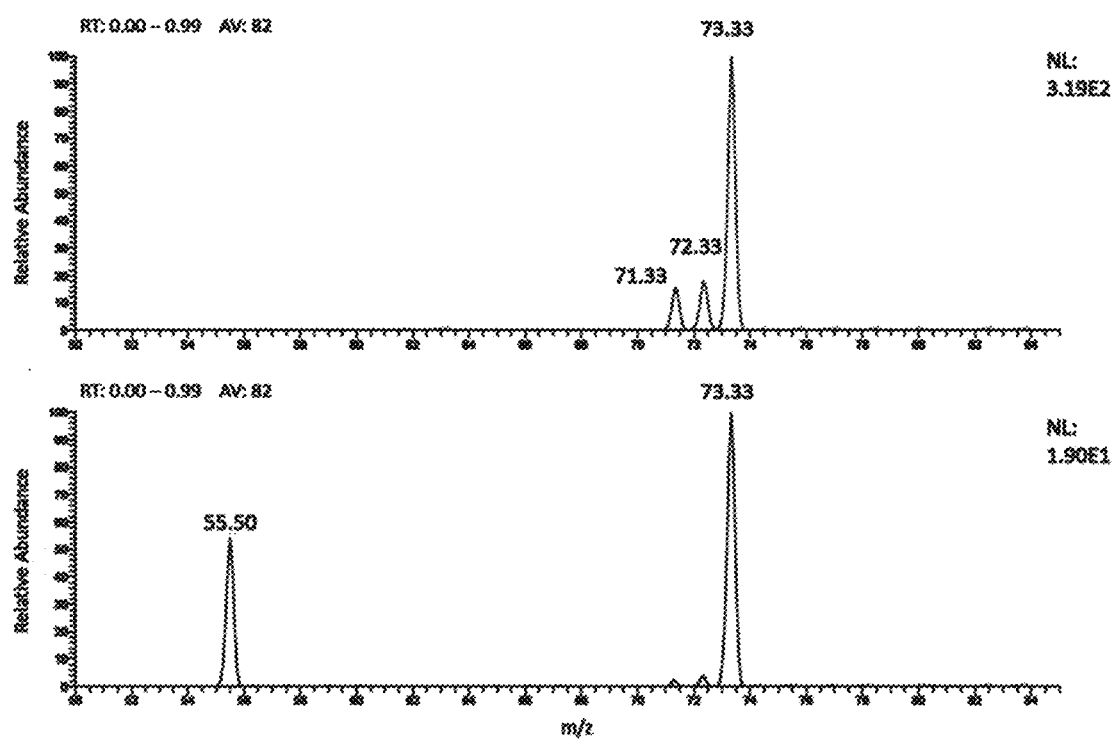
FIG. 6 is a water structure analysis diagram of $(H_2O)_4$ small molecular group water of the present invention.
Figure 7:
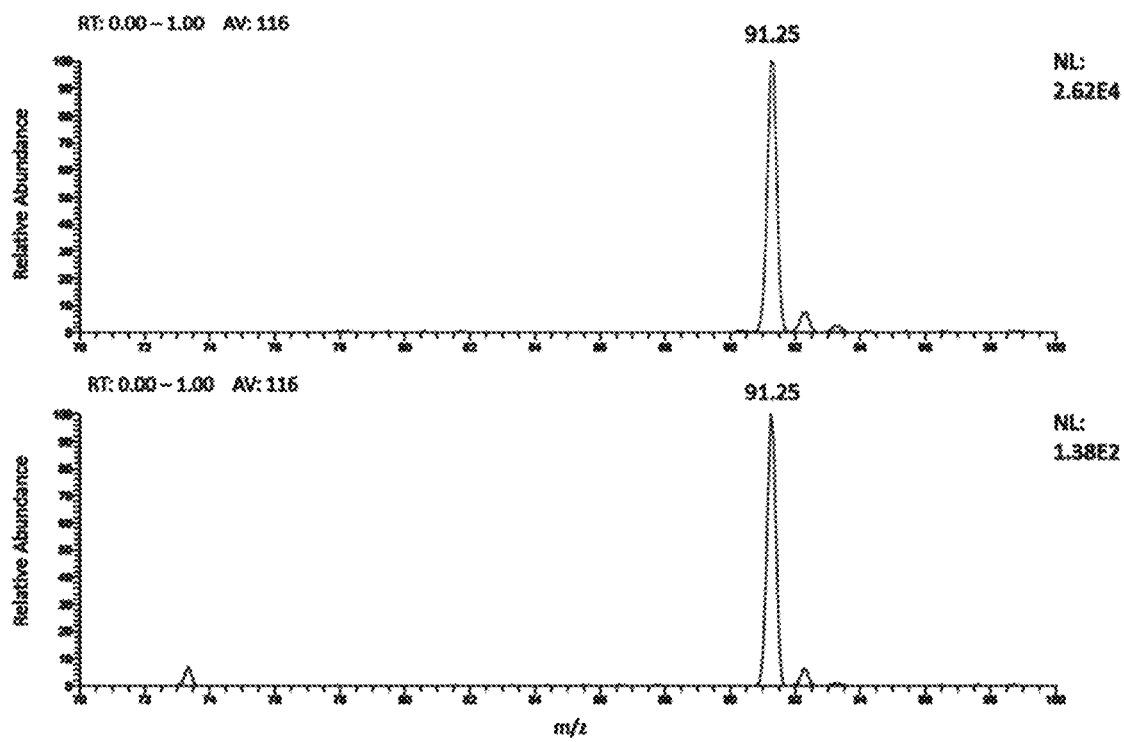
FIG. 7 is a water structure analysis diagram of $(H_2O)_5$ small molecular group water of the present invention.
Figure 8:
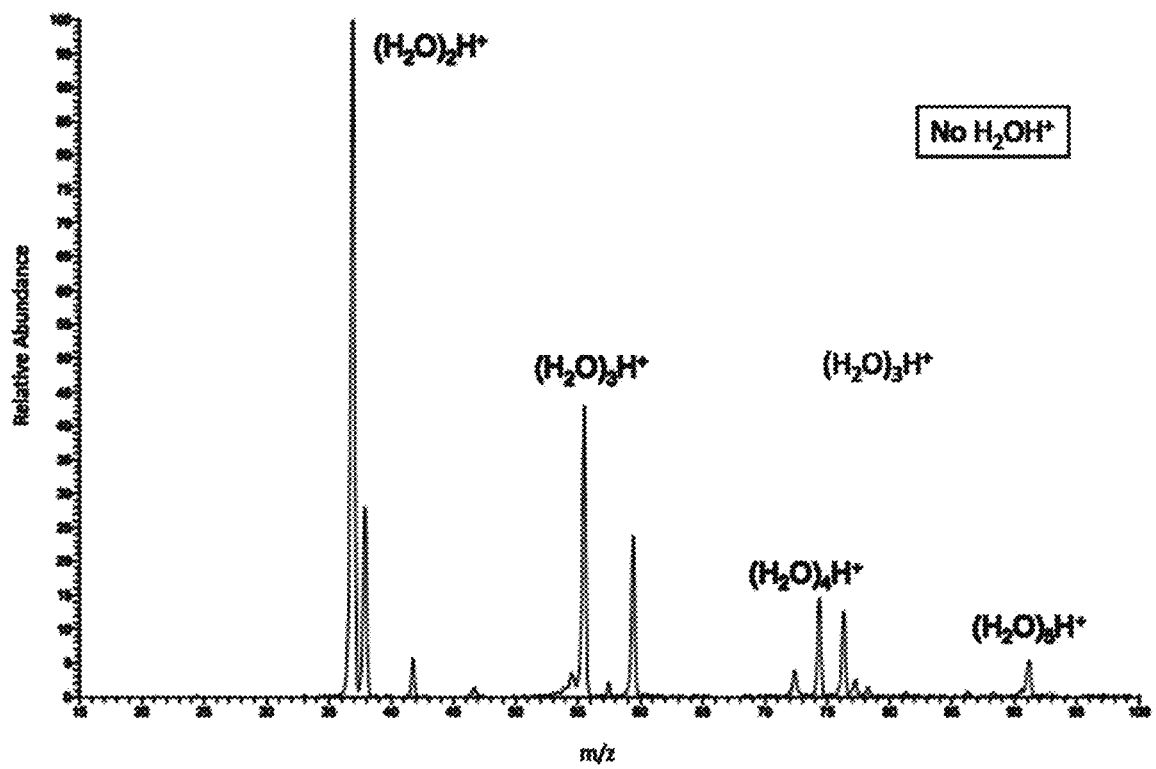
FIG. 8 is a structural analysis and comparison diagram of various small molecular group water of the present invention.
Figure 9:
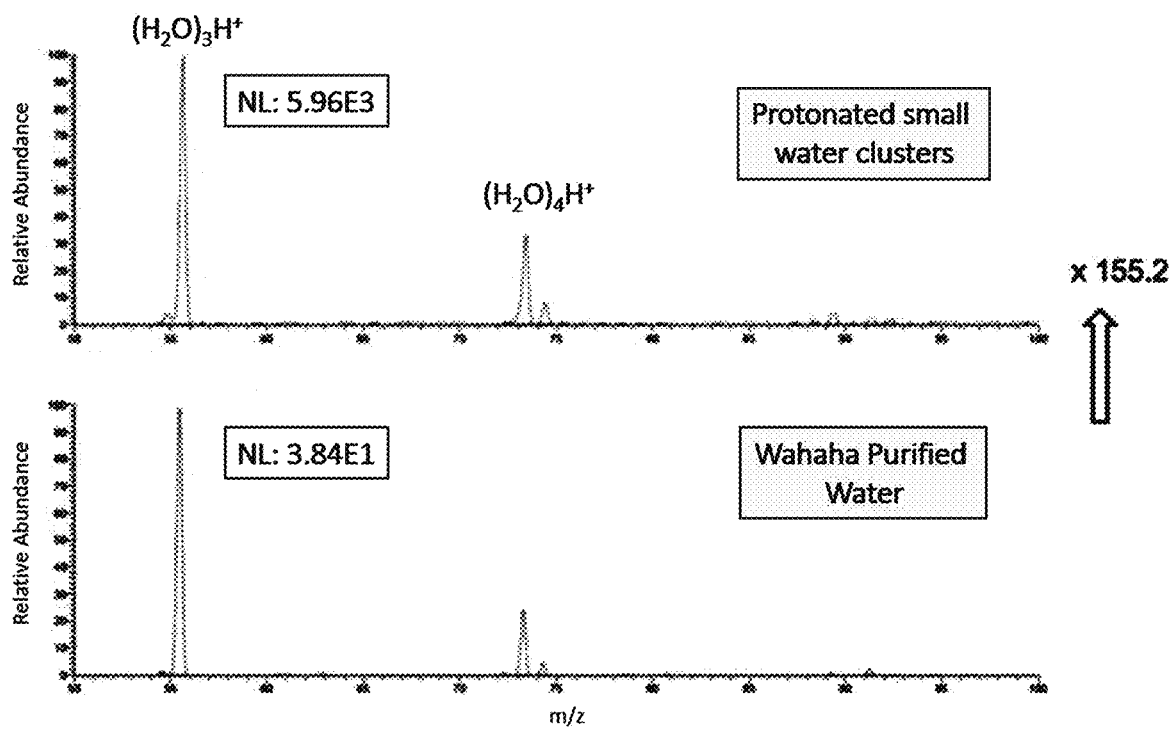
FIG. 9 is a diversion analysis control diagram of commercial drinking water and post-treatment small water.
Figure 10:
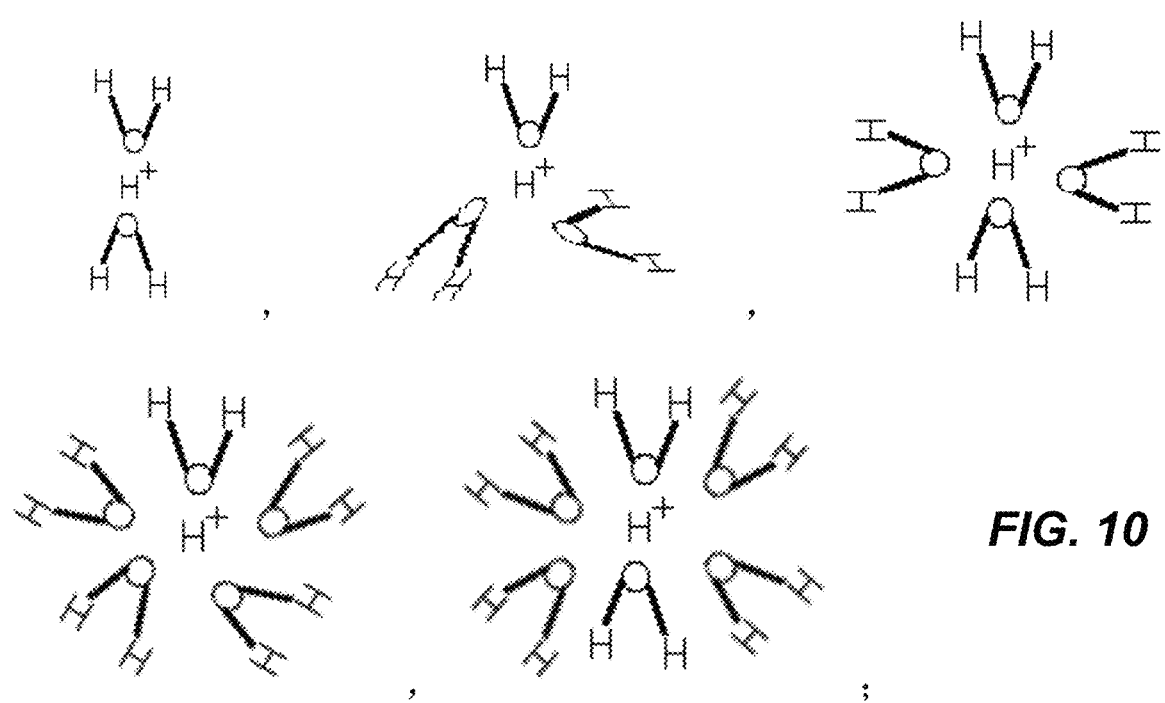
FIG. 10 is a structure diagram of small molecule water that includes 2, 3, 4, 5, or 6 water molecules surrounding a hydrogen ion (H+) according to embodiments of the disclosure.
Figure 11:
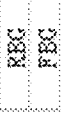
FIG. 11 is a table showing experimental results.

As shown in FIG. 5, a preparation device includes: firstly, ordinary water stored in a water storage bucket 10. The water enters an atomization device 30 through a hydrophobic pump 20 for atomization, and the atomized water is sent to the hydrogen ion generation region 50 through an atomization water channel 60. The atomized water is then mixed in the hydrogen ion and water vapor mixing area 150 of the mixing device 40. As a result, 2, 3, 4, 5, or 6 water molecules around a positively charged hydrogen ion can be obtained. As shown in FIG. 4, the water molecules refer to H$_2$O. That is, relatively stable small molecular clusters are formed from groups of water molecules surrounding a positively charged hydrogen ion H+. The mixing device 40 is separated into a hydrogen ion generation region 50 and the hydrogen ion and water vapor mixing region 150 by a porous cathode 120. In the present application, purified water in the water storage tank 160 is fed into a hollow launching needle 110 through a miniature infusion pump 140. The purified water is ionized by a strong electric field at the tip to form hydrogen ions. Since the radius of the hydrogen ions is extremely small, a strong electric field is formed, and water molecules of atomized water are adsorbed in the hydrogen ions and the water vapor mixing region 150 so as to form 2, 3, 4, 5, and 6 small water clusters. The water is attached to a proton, so that the small molecular group water has hydrogen ion energy. And due to the existence of the electrostatic energy of the hydrogen ions, the small molecule water has a lifetime of more than 4 days In the present embodiment, the hydrogen ion generator 50 refers to the hydrogen ion generation raw material hydrogen 100 being fed into the hydrogen ion generation region 50 via the pump body 130. The needle tip of the hollow launch needle 110 is placed in the hydrogen ion generation region 50, a strong electric field being generated at the needle tip of the hollow launch needle 110, the hydrogen being ionized to form a positively charged hydrogen ion, and the other end of the needle tip of the hollow launch needle 110 being connected to the water storage tank 160.

| Feed liquid (time) | Half peak width |
|---|---|
| Stock solution (July 16th, a year) | 87.1 Hz |
| After treatment (July 16th, a year) | 50.9 Hz |
| After treatment (July 17th, a year) | 50.8 Hz |
| After treatment (July 18th, a year) | 51.5 Hz |
| After treatment (July 19th, a year) | 51.7 Hz |
| After treatment (July 20th, a year) | 62.4 Hz |

As shown in the table above, in 4 days from July 16 to July 19 of a certain year, the half-peak width of $O^{17}$ of the small molecule water is almost kept unchanged, and the lifespan of the small molecular group water is indicated to be greater than 80 hours. After treatment with respect to ordinary drinking water through a conventional method, the display results are as shown in FIG. 2 and FIG. 3.

The small molecule water prepared in the present invention is determined respectively, and, as shown in FIG. 6 and FIG. 7, different numbers of water molecular groups can be obtained.

In the present embodiment, small molecule water is determined, and the comparison diagram of different protonated small water clusters drinking water shown in FIG. 8 can be obtained.

Embodiment 2

According to the method of example 1, the results shown in FIG. 9 can be obtained by comparing the commercially available drinking water with the treated water.

Embodiment 3

According to the small-molecule drinking water disclosed by the invention, relevant volunteers (fasting insulin bias) are used for drinking small-molecule drinking water for two months. Fasting insulin drops from 151.2 to 49.4, and fasting glycosylated hemoglobin drops from 6.2 to 5.3.

Embodiment 4

The data in the above figure show that during the induction period of diabetes, the dosage group (from 16.5 to 17.3) increased by only 0.8, while that of the control group (from 14 to 19.8) increased by 5.8.

During the period of diabetes treatment, the dosage group (decreased from 17.3 to 12.8) decreased by 4.5, while the control group (increased from 19.8 to 2.0) increased by 0.2.

This experiment shows that small molecule water not only has therapeutic effects on diabetes, but also has preventive effects, as shown in FIG. 11.

Embodiment 5

According to the small-molecule drinking water disclosed by the invention, the triglycerides of the related volunteers have been more than 5 for more than 20 years, and the triglycerides have been reduced from 5.03 to 2.52 after drinking 500 CC of protonated small water clusters drinking water every day for 4 weeks.

The invention claimed is:

1. A method, comprising:

atomizing water by means of an atomization device (30) to generate atomized water vapor;

feeding the atomized water vapor into a hydrogen ion generation region (50) by means of an atomization water channel (60);

providing a needle tip of a hollow emission needle (110) placed in the hydrogen ion generation region (50);

generating an electric field at a needle tip of the hollow emission needle (110), the electric field ionizing the atomized water vapor to form positively charged hydrogen ions (H+); and mixing the hydrogen ions with the water vapor in a mixing region (150) of the mixing device (40) to obtain small-molecule drinking water with 2, 3, 4, 5, or 6 water molecules around a positively charged hydrogen ion (H+), the mixing device (40) being divided into a hydrogen ion generation area (50) and a hydrogen ion and water vapor mixing area (150) by a perforated cathode (120) in the mixing device (40).

2. The method according to claim 1, wherein the water is purified water, wherein the purified water is placed in a sterile water storage bucket (10), and wherein the purified water is atomized by means of a sterile infusion pump (20) pumping the purified water to the atomization device (30).

3. The method according to claim 1, further comprising:

feeding, raw material hydrogen (100) into the hydrogen ion generation region (50) through a pump body (130) and via a needle tip of the hollow emission needle (110) placed in the hydrogen ion generation region (50);

generating an electric field at the needle tip of the hollow emission needle (110), the needle tip ionizing the hydrogen to form positively charged hydrogen ions, wherein the hollow emission needle (110) is connected with a water storage tank (160) that provides a source of the purified water.

4. The method according to claim 1, further comprising:

conveying, by the micro infusion pump (140), purified water in a water storage tank (160) to the needle tip of the hollow emission needle (110), supplying the needle tip of the hollow emission needle (110) and the perforated cathode (120) with a voltage by means of a high-voltage power supply (90);

generating an electric field is at the needle tip of the hollow emission needle (110); and ionizing water molecules at the needle tip of the hollow emission needle (110) to form positively charged hydrogen ions.

5. The method according to claim 1, further comprising maintaining, in an internal space of the atomizing device (30) and the mixing device (40), a temperature above 80 DEG C.

6. A method of producing drinking water, comprising:

generating positive hydrogen ions (H+) at least in part by passing water through a hollow emission needle charged to a high voltage;

mixing the positive hydrogen ions (H+) with atomized water to create small molecule water containing a plurality of small molecule water clusters, each of the plurality of small molecule water clusters including a single positive hydrogen ion (H+) surrounded by 2, 3, 4, 5, or 6 water ($H_2O$) molecules; and collecting the small molecule water in a container.

7. The method of claim 6, wherein the hollow emission needle extends into a hydrogen ion generation region, and wherein generating positive hydrogen ions (H+) is further performed by feeding raw material hydrogen into the hydrogen ion generation region.

8. The method of claim 7, wherein mixing the positive hydrogen ions (H+) with the atomized water includes creating the small molecule water with a concentration of positive hydrogen ions (H+) that is not less than $10^{-6}$ mol/L.

9. The method of claim 8, wherein mixing the positive hydrogen ions (H+) with the atomized water is performed at a temperature above 80 degrees-C.

10. The method of claim 7, further comprising producing the atomized water by pumping purified water from a storage tank to an atomization device.

11. The method of claim 10, wherein producing the atomized water includes maintaining the atomization device at a temperature of at least 80 degrees-C.

12. The method of claim 7, further comprising electrically coupling a high-voltage power supply between the hollow emission needle and a cathode.

13. The method of claim 12, further comprising providing a water storage tank as a source of the water passed through a hollow emission needle, and electrically coupling the water storage tank to the hollow emission needle.

* * * * *